US008658426B2

(12) United States Patent
Timken et al.

(10) Patent No.: US 8,658,426 B2
(45) Date of Patent: Feb. 25, 2014

(54) MONITORING OF IONIC LIQUID CATALYST DEACTIVATION

(75) Inventors: Hye-Kyung Timken, Albany, CA (US); Annie T. Pathiparampil, Orinda, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 553 days.

(21) Appl. No.: 12/437,515

(22) Filed: May 7, 2009

(65) Prior Publication Data

US 2010/0129921 A1  May 27, 2010

Related U.S. Application Data

(60) Provisional application No. 61/118,209, filed on Nov. 26, 2008.

(51) Int. Cl.
| | |
|---|---|
| *G01N 31/10* | (2006.01) |
| *G01N 31/16* | (2006.01) |
| *B01J 27/125* | (2006.01) |
| *B01J 27/06* | (2006.01) |
| *B01J 31/00* | (2006.01) |

(52) U.S. Cl.
CPC ............... *G01N 31/10* (2013.01); *G01N 31/16* (2013.01); *B01J 27/125* (2013.01); *B01J 27/06* (2013.01); *B01J 31/00* (2013.01)
USPC ............... 436/37; 502/53; 502/167; 502/150; 502/231; 502/224

(58) Field of Classification Search
None
See application file for complete search history.

(56) References Cited

U.S. PATENT DOCUMENTS

| | | | |
|---|---|---|---|
| 6,096,553 A * | 8/2000 | Heald et al. ............... | 436/40 |
| 7,432,408 B2 | 10/2008 | Timken et al. | |
| 7,432,409 B2 | 10/2008 | Elomari et al. | |
| 2007/0142211 A1 | 6/2007 | Elomari et al. | |
| 2007/0142213 A1 | 6/2007 | Elomari et al. | |
| 2007/0142216 A1 | 6/2007 | Harris et al. | |
| 2007/0142217 A1 | 6/2007 | Elomari et al. | |
| 2007/0142218 A1 | 6/2007 | Harris et al. | |
| 2007/0142676 A1 | 6/2007 | Elomari et al. | |
| 2007/0249485 A1 | 10/2007 | Elomari et al. | |

OTHER PUBLICATIONS

Cima et al. "The Generalized Lewis Acid-Base Titration of Palladium and Niobium". 1988. Metallurgical Transactions B. vol. 19B. pp. 893-917.*

(Continued)

*Primary Examiner* — Robert Xu
(74) *Attorney, Agent, or Firm* — Susan M. Abernathy (57) ABSTRACT

A process for determining ionic liquid catalyst deactivation including (a) collecting at least one sample of an ionic liquid catalyst; (b) hydrolyzing the at least one sample to provide at least one hydrolyzed sample; (c) titrating the at least one hydrolyzed sample with a basic reagent to determine a volume of the basic reagent necessary to neutralize a Lewis acid species of the ionic liquid catalyst; and (d) calculating the acid content of the at least one sample from the volume of basic reagent determined in step (c) is described. Processes incorporating such a process for determining ionic liquid catalyst deactivation are also described. These processes are an alkylation process, a process for controlling ionic liquid catalyst activity in a reaction producing by-product conjunct polymers, and a continuous process for maintaining the acid content of an ionic liquid catalyst at a target acid content in a reaction producing by-product conjunct polymers.

24 Claims, 3 Drawing Sheets

(56) References Cited

OTHER PUBLICATIONS

Harjani et al. "Lewis acidic ionic liquids for the synthesis of electrophilic alkenes via the Knoevenagel condensation". 2002. Tetrahedron letters. vol. 43. pp. 1127-1130.*

U.S. Appl. No. 12/003,577, "System and Apparatus for Ionic Liquid Catalyst Regeneration," filed Dec. 28, 2007, Luo et al.

U.S. Appl. No. 12/099,480, "Regeneration of Ionic Liquid Catalyst Using a Regeneration Metal in the Presence of Added Hydrogen" filed Dec. 20, 2005, Harris et al.

Wu et al., Studies on acidity of chloroaluminate ionic liquids and its catalytic performance for alkylation of benzene with long-chain alkenes, PubMed, Mar. 2007, 27(3) 460-4.

* cited by examiner

MONITORING OF IONIC LIQUID CATALYST DEACTIVATION

This application claims the benefit of provisional Application No. 61/118,209, filed Nov. 26, 2008, herein incorporated in its entirety.

FIELD OF ART

The processes described herein relate to determining ionic liquid catalyst deactivation. More particularly, the processes described herein involve determining ionic liquid catalyst deactivation by titrating one or more samples of the ionic liquid catalyst with a basic reagent.

BACKGROUND

An alkylation process, which is disclosed in U.S. Pat. No. 7,432,408 ("the '408 publication"), involves contacting isoparaffins, preferably isopentane, with olefins, preferably ethylene, in the presence of an ionic liquid catalyst to produce gasoline blending components. The contents of the '408 patent are incorporated by reference herein in its entirety.

An ionic liquid catalyst distinguishes this novel alkylation process from conventional processes that convert light paraffins and light olefins to more lucrative products such as the alkylation of isoparaffins with olefins and the polymerization of olefins. For example, two of the more extensively used processes to alkylate isobutane with $C_3$-$C_5$ olefins to make gasoline cuts with high octane numbers use sulfuric acid ($H_2SO_4$) and hydrofluoric acid (HF) catalysts.

As a result of use, ionic liquid catalysts can become deactivated, i.e. lose activity, and may eventually need to be replaced. Alkylation processes utilizing an ionic liquid catalyst can form by-products known as conjunct polymers. These conjunct polymers generally deactivate the ionic liquid catalyst by forming complexes with the ionic liquid catalyst. Conjunct polymers are highly unsaturated molecules and can complex the Lewis acid portion of the ionic liquid catalyst via their double bonds. For example, as aluminum trichloride in aluminum trichloride-containing ionic liquid catalysts becomes complexed with conjunct polymers, the activity of these ionic liquid catalysts becomes impaired or at least compromised. Conjunct polymers may also become chlorinated and through their chloro groups may interact with aluminum trichloride in aluminum trichloride-containing catalysts and therefore reduce the overall activity of these catalysts or lessen their effectiveness as catalysts for their intended purpose.

Accordingly, there is a need for a method for determining ionic liquid catalyst deactivation so that deactivated ionic liquid catalysts can be effectively and efficiently replaced when appropriate.

SUMMARY

Disclosed herein is a process for determining ionic liquid catalyst deactivation. The process comprises: (a) collecting at least one sample of an ionic liquid catalyst; (b) hydrolyzing the at least one sample to provide at least one hydrolyzed sample; (c) titrating the at least one hydrolyzed sample with a basic reagent to determine a volume of the basic reagent necessary to neutralize a Lewis acid species of the ionic liquid catalyst; and (d) calculating the acid content of the at least one sample from the volume of basic reagent determined in step (c).

Also disclosed herein are processes utilizing an embodiment of the process for determining ionic liquid catalyst deactivation as disclosed herein. They include an alkylation process that determines ionic liquid catalyst deactivation, a process for controlling ionic liquid catalyst activity in a reaction producing by-product conjunct polymers, and a continuous process for maintaining the acid content of an ionic liquid catalyst at a target acid content in a reaction producing by-product conjunct polymers.

In one embodiment, an alkylation process comprises: (a) reacting isoparaffins with olefins in the presence of an ionic liquid catalyst to provide a hydrocarbon product; (b) collecting samples of the ionic liquid catalyst at regular intervals; (c) hydrolyzing the samples to provide hydrolyzed samples; (d) titrating the hydrolyzed samples with a basic reagent to determine a volume of the basic reagent necessary to neutralize a Lewis acid species of each sample; (e) calculating the acid content of each sample from the volume of basic reagent determined in step (d); and (f) regenerating the ionic liquid catalyst when the acid content reaches a predetermined level to provide a regenerated ionic liquid catalyst.

In another embodiment, a process for controlling ionic liquid catalyst activity in a reaction producing by-product conjunct polymers comprises: (a) using an ionic liquid catalyst in a reaction producing by-product conjunct polymers; (b) collecting samples of the ionic liquid catalyst at regular intervals; (c) hydrolyzing the samples to provide hydrolyzed samples; (d) titrating the hydrolyzed samples with a basic reagent to determine a volume of the basic reagent necessary to neutralize a Lewis acid species of each sample; (e) calculating the acid content of each sample from the volume of basic reagent determined in step (d); and (f) regenerating the ionic liquid catalyst when the acid content reaches a predetermined level to provide a regenerated ionic liquid catalyst.

In yet another embodiment, a continuous process for maintaining the acid content of an ionic liquid catalyst at a target acid content in a reaction producing by-product conjunct polymers comprises: (a) using an ionic liquid catalyst in a reaction producing by-product conjunct polymers; (b) collecting samples of the ionic liquid catalyst at regular intervals; (c) hydrolyzing the samples to provide hydrolyzed samples; (d) titrating the hydrolyzed samples with a basic reagent to determine a volume of the basic reagent necessary to neutralize a Lewis acid species of each sample; (e) calculating the acid content of each sample from the volume of basic reagent determined in step (d); and (f) varying one or more conditions of the reaction if the acid content is above or below a target acid content to maintain the acid content at the target acid content.

Among other factors, it has been discovered that titration can be used as a technique to successfully monitor the deactivation level of an ionic liquid catalyst. The use of titration in the process for determining ionic liquid catalyst deactivation as disclosed herein enables commercial exploitation of ionic liquid catalysts in alkylation and other chemical processes employing ionic liquid catalysts during which ionic liquid catalysts become deactivated. Due to such deactivation, these chemical processes require monitoring ionic liquid catalyst deactivation in order to maintain sufficient reaction. Ionic liquid catalysts are also expensive to replace. Thus, the use of ionic liquid catalysts in these chemical processes is economically feasible only when the catalysts can be efficiently regenerated and recycled. The process for determining ionic liquid catalyst &activation as disclosed herein and the other processes utilizing an embodiment of such process for determining ionic liquid catalyst deactivation can maintain sufficient reaction during ionic liquid deactivating chemical processes.

The present processes can also permit efficient regeneration of ionic liquid catalysts and recycling of such regenerated catalysts.

DETAILED DESCRIPTION

Process for Determining Ionic Liquid Catalyst Deactivation

Disclosed herein is a process for determining ionic liquid catalyst deactivation. According to such process, at least one sample of an ionic liquid catalyst is collected. The at least one sample is then hydrolyzed to provide at least one hydrolyzed sample. Thereafter, the at least one hydrolyzed sample is titrated with a basic reagent to determine a volume of the basic reagent necessary to neutralize a Lewis acid species of the ionic liquid catalyst. Subsequently, the acid content of the at least one sample is calculated from the volume of basic reagent determined above.

Titration is a technique known in the art used to determine an unknown concentration of a known reactant. An acid-base titration, like the one utilized in the present process, can determine an unknown concentration of a particular acid by neutralizing the acid with a particular base. Such an acid-base titration involves adding base having a known concentration to a known volume of acid having an unknown concentration. When the base neutralizes the acid, as indicated for example by an indicator, addition of base stops and the volume of base required for the neutralization reaction is known. The chemical equation for the neutralization reaction between the particular acid and particular base is also known. Thus, the concentration of the acid can be calculated from the number of moles of base X that combine with the number of moles of acid Y in the chemical equation, the concentration of base, the volume of base, and the volume of acid:

Concentration of acid=($X$*concentration of base*volume of base)/($Y$*volume of acid)

In the present process, the acid is the Lewis acid species present in the ionic liquid catalyst and the base is the basic reagent. While titration is a basic analytical technique, the inventors of the present application have discovered titration of ionic liquid catalyst with a basic reagent is a particularly useful and effective process for determining ionic liquid catalyst deactivation.

The present process is based in part on the discovery that an ionic liquid catalyst deactivation mechanism is the formation of by-products known as conjunct polymers.

The conjunct polymers can deactivate ionic liquid catalysts by forming complexes with or simply interacting with the ionic liquid catalyst. It is believed that complexes form because conjunct polymers, by virtue of their double bonds, form pi ($\pi$) complexes with or sigma ($\sigma$) bonds with the Lewis acid species, such as metal halides, in the ionic liquid catalyst. As an example, conjunct polymers can complex with $AlCl_3$, a Lewis acid present in chloroaluminate ionic liquid catalysts such as 1-butyl-pyridinium heptachloroaluminate. Conjunct polymers may complex $AlCl_3$ via their double bonds to make reversible pi-complexes. The pi-complexes may convert to irreversible sigma-complexes. Conjunct polymers with their cationic character may also complex chloroaluminate species resulting in more deactivating complexes.

The term "conjunct polymer" as used herein refers to a polymeric compound that might bond to a cationic species of an ionic liquid catalyst by pi bonding or sigma bonding or other means, which results in the polymeric compound binding to the catalyst, so that it is not removable by simple hydrocarbon extraction.

The term conjunct polymer was first used by Pines and Ipatieff to distinguish these polymeric molecules from the usual polymers. Unlike typical polymers, conjunct polymers are polyunsaturated cyclic, polycyclic and acyclic molecules formed by concurrent acid-catalyzed reactions including, among others, polymerization, alkylation, cyclization, and hydride transfer reactions. Conjunct polymers consist of an unsaturated intricate network of molecules that may include one or a combination of 4-, 5-, 6- and 7-membered rings and some aromatic entities in their skeletons. Some examples of the likely polymeric species were reported by Miron et al. (*Journal of Chemical and Engineering Data*, 1963) and Pines (*Chem. Tech*, 1982), which documents are incorporated by reference in their entirety herein. These molecules contain double and conjugated bonds in intricate structures containing a combination of cyclic and acyclic skeletons.

In practice, conjunct polymers are also called "red oils" due to their color and "acid-soluble oils" due to their high uptake in the catalyst phase where saturated hydrocarbons and paraffinic products are usually immiscible.

Conjunct polymers can reduce the activity of the catalyst by two mechanisms. Increasing amounts of conjunct polymers dilute the active components of the ionic liquid catalyst. Additionally, the conjunct polymers bind or otherwise interact with the Lewis acid species (e.g. $AlCl_3$) in the ionic liquid catalyst forming complexes and weakening the acid strength of the catalyst. The two mechanisms can eventually render the catalyst ineffective for influencing reactions, such as an alkylation reaction between isoparaffins and olefins.

Accordingly, ionic liquid catalyst deactivation is a function of the concentration of the Lewis acid species (e.g. $AlCl_3$), which are not bound to or otherwise interacting with conjunct polymers and, therefore, have not formed complexes with conjunct polymers. As the concentration of conjunct polymers in the ionic liquid phase increases, the concentration of free Lewis acid species decreases and catalyst activity decreases. Thus, it has been discovered that measuring the concentration of free Lewis acid species is a way of measuring ionic liquid catalyst deactivation.

As discussed above, in the present process, at least one sample of ionic liquid catalyst is hydrolyzed. Hydrolyzing the ionic liquid catalyst provides at least one hydrolyzed sample, which includes protons. The resultant at least one hydrolyzed sample with its protons is then titrated with a basic reagent. During the titration step, the basic reagent reacts with the protons of the at least one hydrolyzed sample. From the titration, a volume of the basic reagent necessary to neutralize a Lewis acid species of the ionic liquid catalyst is determined. From this volume of basic reagent, the acid content of the at least one sample is calculated. As a result, ionic liquid catalyst deactivation, which corresponds to the concentration of the free Lewis acid species can be determined.

As an example, the ionic liquid catalyst N-butylpyridinium heptachloroaluminate contains the free Lewis acid species, $AlCl_3$. In particular, 1 mole of N-butylpyridinium heptachloroaluminate contains 2 mole $AlCl_3$. Hydrolyzing 1 mole of N-butylpyridinium heptachloroaluminate provides 6 moles of protons, [H]$^+$. Titrating this hydrolyzed N-butylpyridinium heptachloroaluminate with a basic reagent provides the volume of basic reagent necessary to neutralize the AlCl$_3$. Since each mole of AlCl$_3$ requires 3 moles of [OH]$^-$ for titration, and the volume of basic reagent necessary to neutralize the AlCl$_3$ is known, the acid content of the N-butylpyridinium heptachloroaluminate can be calculated as in any acid-base titration.

The process for determining ionic liquid catalyst deactivation, as described herein, is unexpectedly advantageous over other possible processes for determining ionic liquid catalyst deactivation. In particular, the process for determining ionic liquid catalyst deactivation, as described herein, is unexpectedly advantageous over both measuring catalyst density and analyzing a particular element of the catalyst to determine ionic liquid catalyst deactivation.

Ionic liquid catalyst deactivation can be determined indirectly by measuring catalyst density. As discussed above, deactivation occurs via dilution of the catalyst by conjunct polymers. The density of conjunct polymers is less than the density of the ionic liquid catalyst, when free from conjunct polymers. As conjunct polymers accumulate in the catalyst phase, catalyst density decreases. Thus, catalyst density decreases upon catalyst deactivation.

While an on-line instrument such as a coriolis meter or densitomer may continuously monitor catalyst density, using catalyst density to determine ionic liquid catalyst deactivation can be problematic at times. Operational changes in the process in which the ionic liquid catalyst is used may alter the conjunct polymer. Such changes in the conjunct polymer render catalyst density an unreliable measurement. Accordingly, caution must be exercised in correlating catalyst density with ionic liquid catalyst deactivation.

Elemental analysis of a key element in the catalyst is another useful method for determining ionic liquid catalyst deactivation. However, analyzing a particular element of the catalyst to determine ionic liquid catalyst deactivation can also be problematic at times. For example, aluminum content of a chloroaluminate ionic liquid catalyst corresponds to catalyst deactivation. However, measuring aluminum content is time consuming. Measuring aluminum content accurately is also difficult because the ionic liquid catalyst is sensitive to the atmospheric moisture.

The present process of determining ionic liquid catalyst deactivation does not suffer from the shortcomings associated with measuring catalyst density and elemental analysis. Titration provides accurate measurements of the concentration of the Lewis acid species, whether or not there are operational changes in the process that the ionic liquid catalyst catalyzes. A very small sample size (e.g. less, than 1 gram) of ionic liquid can be accurately titrated. Furthermore, titration can be conducted quickly (e.g. within an hour of sample collection). Moreover, with titration, simple procedural safeguards can be taken to protect the ionic liquid catalyst from exposure to the atmosphere.

Conjunct polymers form during a variety of reactions in which ionic liquid catalysts are employed, for example, alkylation, polymerization, dimerization, oligomerization, acetylation, olefin metathesis, and copolymerization. The alkylation may be paraffin alkylation or aromatic alkylation. Conjunct polymers also form during olefin isomerization, desulfurization, and catalytic cracking. Additionally, conjunct polymers are by-products of many types of Friedel-Crafts reactions, which are reactions that fall within the broader category of electrophylic substitution, like alkylation and acylation. Accordingly, the present process is useful for determining deactivation of an ionic liquid catalyst that has been used to catalyze any of these above-mentioned reactions.

In one embodiment, the ionic liquid catalyst has been used to catalyze a reaction selected from the group consisting of paraffin alkylation, aromatic alkylation, polymerization, dimerization, oligomerization, acetylation, olefin metathesis, copolymerization, olefin isomerization, desulfurization, catalytic cracking, acylation and combinations thereof.

In one embodiment, the ionic liquid catalyst has been used to catalyze a Friedel-Crafts reaction. In another embodiment, the Friedel-Crafts reaction is alkylation.

The process for determining ionic liquid catalyst deactivation, as described herein, can further include a step in which the acid content of the at least one sample is compared to a predetermined value. With such a comparison step, the present process may be used to monitor deactivation of an ionic liquid catalyst in a chemical process (e.g. alkylation) over time or may be used to monitor the quality of ionic liquid catalyst made during a catalyst manufacturing process.

In one embodiment, the predetermined value can be a percentage of the acid content of a fresh ionic liquid catalyst. In another embodiment, the predetermined value can be about 80% of the acid content of a fresh ionic liquid catalyst. As used herein, the term "fresh ionic liquid catalyst" refers to ionic liquid catalyst that has not been subject to deactivation. These embodiments are especially useful for monitoring deactivation of an ionic liquid catalyst in a chemical process (e.g. alkylation) over time.

Accordingly, the ionic liquid catalyst utilized in the present process can be a catalyst which has been used in a reaction that produces by-product conjunct polymers and is therefore at least partially deactivated. In this case, the titration process is used to determine the level of deactivation of this at least partially deactivated catalyst. When the catalyst's deactivation level reaches a predetermined level, the ionic liquid catalyst can be regenerated.

In one embodiment, the predetermined value can be the acid content of fresh ionic liquid catalyst. In another embodiment, the predetermined value can be a predetermined acid content. These embodiments are particularly useful for monitoring the quality of ionic liquid catalyst made during a catalyst manufacturing process.

Accordingly, the ionic liquid catalyst utilized in the present process can be a fresh ionic liquid catalyst. Such fresh ionic liquid catalyst can be newly synthesized. In this manner, the present process can be used for quality control purposes.

Importantly, the at least one sample of an ionic liquid catalyst collected may be a plurality of samples collected at regular intervals from a reaction employing the ionic liquid catalyst. In this manner, the present process is useful for monitoring ionic liquid catalyst deactivation. For example, the plurality of samples collected at regular intervals may originate from ionic liquid catalyst used in a chemical reaction producing by-product conjunct polymers (e.g. alkylation). As such, the present process can be used to monitor ionic liquid catalyst deactivation during a chemical reaction catalyzed by the ionic liquid catalyst. As another example, the plurality of samples collected at regular intervals may originate from ionic liquid catalyst produced in a catalyst manufacturing process. As such, the present process can be used to monitor the quality of ionic liquid catalyst produced in a catalyst manufacturing process.

In the present process, the sample(s) of the ionic liquid catalyst collected may be less than 1 gram. The sample(s) titrated may also be less than 1 gram.

The basic reagent may be a hydroxide of a Group IA metal or a Group IIA metal, including potassium hydroxide (KOH), sodium hydroxide (NaOH), rubidium hydroxide (RbOH), cesium hydroxide (CsOH), and barium hydroxide ($BaOH_2$). In one embodiment, the basic reagent is selected from the group consisting of potassium hydroxide, sodium hydroxide, rubidium hydroxide, cesium hydroxide, and barium hydroxide. In another embodiment, the basic reagent is potassium hydroxide.

Alkylation Process

The process for determining ionic liquid catalyst deactivation can be used in an alkylation process. In one embodiment, the alkylation process first involves reacting isoparaffins with olefins in the presence of an ionic liquid catalyst to provide a hydrocarbon product. As used herein, the term "isoparaffin" means any branched-chain saturated hydrocarbon compound, i.e., a branched-chain alkane with a chemical formula of $C_nH_{2n+2}$. Examples of isoparaffins are isobutane and isopentane. The term "olefin," as used herein, means any unsaturated hydrocarbon compound having at least one carbon-to-carbon double bond, i.e., an alkene with a chemical formula of $C_nH_{2n}$. Examples of olefins include ethylene, propylene, butene, and so on.

This embodiment further involves collecting samples of the ionic liquid catalyst at regular intervals and hydrolyzing the samples to provide hydrolyzed samples. The alkylation process then involves titrating the hydrolyzed samples with a basic reagent to determine a volume of the basic reagent necessary to neutralize a Lewis acid species of each sample. The acid content of each sample is then calculated from the volume of basic reagent as determined above. Thereafter, the alkylation process includes regenerating the ionic liquid catalyst when the acid content reaches a predetermined level to provide a regenerated ionic liquid catalyst.

As used herein, the term "regenerated ionic liquid catalyst" refers to ionic liquid catalyst that is either fully regenerated or partially regenerated. Fully regenerated ionic liquid catalyst is substantially free from conjunct polymer-metal halide complexes. Partially regenerated ionic liquid catalyst still includes conjunct polymer-metal halide complexes such that it is not substantially free from conjunct polymer-metal halide complexes. In the present alkylation process, the regenerated ionic liquid catalyst is typically fully regenerated.

Various methods of regenerating an ionic liquid catalyst are known in the art. Such methods are described in detail in U.S. Patent Application Publication Nos. 2007/0142218, 2007/0142217, 2007/0142215, 2007/0142214, 2007/0142213, 2007/142211, 2007/0142216, 2007/0249486, and 2007/024985 and a provisional U.S. patent application entitled "Electrochemical Removal of Conjunct Polymers from Chloroaluminate Ionic Liquids," which is being filed concurrently with the present application. These documents are incorporated by reference in their entirety herein.

Process for Controlling Ionic Liquid Catalyst Activity in a Reaction Producing By-Product Conjunct Polymers As discussed above, a variety of chemical reactions produce by-product conjunct polymers when catalyzed by ionic liquid catalysts. By-product conjunct polymers are not limited to ionic liquid catalyzed alkylation processes only. Reactions that produce by-product conjunct polymers when catalyzed by ionic liquid catalysts include paraffin alkylation, aromatic alkylation, polymerization, dimerization, oligomerization, acetylation, olefin metathesis, copolymerization, olefin isomerization, desulfurization, catalytic cracking, and Friedel-Crafts reactions such as alkylation and acylation. Any ionic liquid catalyzed reaction that produces by-product conjunct polymers is subject to ionic liquid catalyst deactivation. Therefore, the above-described process for determining ionic liquid catalyst deactivation is useful for controlling ionic liquid catalyst activity in such reactions.

In one embodiment, a process for controlling ionic liquid catalyst activity in a reaction producing by-product conjunct polymers involves using an ionic liquid catalyst in a reaction producing by-product conjunct polymers and collecting samples of the ionic liquid catalyst at regular intervals. Such process further involves hydrolyzing the samples to provide hydrolyzed samples and titrating the hydrolyzed samples with a basic reagent to determine a volume of the basic reagent necessary to neutralize a Lewis acid species of each sample. Thereafter, such process involves calculating the acid content of each sample from the volume of basic reagent determined above and regenerating the ionic liquid catalyst when the acid content reaches a predetermined level to provide a regenerated ionic liquid catalyst.

Continuous Process for Maintaining Acid Content of an Ionic Liquid Catalyst at a Target Acid Content in a Reaction Producing By-Product Conjunct Polymers The process for determining ionic liquid catalyst deactivation can also be used in a continuous ionic liquid catalyzed process that produces by-product conjunct polymers. During such a continuous ionic liquid catalyzed process, it is desirable to maintain acid content of an ionic liquid catalyst at a target acid content. Such maintenance of ionic liquid catalyst acid content provides a steady-state reaction, including a steady reaction rate and a steady reaction yield.

Accordingly, in one embodiment, a continuous process for maintaining acid content of an ionic liquid catalyst at a target acid content in a reaction producing by-product conjunct polymers involves using an ionic liquid catalyst in a reaction producing by-product conjunct polymers and collecting samples of the ionic liquid catalyst at regular intervals. Such process further involves hydrolyzing the samples to provide hydrolyzed samples and titrating the hydrolyzed samples with a basic reagent to determine a volume of the basic reagent necessary to neutralize a Lewis acid species of each sample. Thereafter, such process involves calculating the acid content of each sample from the volume of basic reagent determined above and varying one or more conditions of the reaction if the acid content is above or below a target acid content.

The condition varying step of the continuous process maintains the acid content of the ionic liquid catalyst at the target acid content. The target acid content may be a predetermined value or predetermined level. However, the target acid content may be a range of predetermined values or predetermined levels.

The condition varying step may also occur if the acid content is a particular amount, for example, a particular percentage above or below the target acid content.

During the condition varying step, fresh ionic liquid catalyst may be added to the reaction, the rate at which fresh ionic liquid catalyst is added may be changed, used ionic liquid catalyst may be removed from the reaction, or the rate at which used ionic liquid catalyst is removed from the reaction may be changed. During the condition varying step, regenerated ionic liquid catalyst may be added to the reaction or the rate at which ionic liquid catalyst is regenerated may be changed. Thus, the one or more conditions varied may be selected from the group consisting of adding fresh ionic liquid catalyst to the reaction, a rate of fresh ionic liquid catalyst added to the reaction, removing used ionic liquid catalyst from the reaction, a rate of removing used ionic liquid catalyst from the reaction, adding regenerated ionic liquid catalyst to the reaction, a rate at which the ionic liquid catalyst is regenerated, and combinations thereof.

Ionic Liquid Catalyst

Any type of ionic liquid catalyst may be utilized in the processes described herein. Ionic liquid catalysts are well known in the art.

As used herein, the term "ionic liquids" refers to liquids that are composed entirely of ions as a combination of cations and anions. The term "ionic liquids" includes low-temperature ionic liquids, which are generally organic salts with melting points under 100° C. and often even lower than room temperature.

Ionic liquids may be suitable, for example, for use as a catalyst and as a solvent in alkylation and polymerization reactions as well as in dimerization, oligomerization, acylation, olefin metathesis, and copolymerization reactions.

One class of ionic liquids is fused salt compositions, which are molten at low temperature and are useful as catalysts, solvents, and electrolytes. Such compositions are mixtures of components, which are liquid at temperatures below the individual melting points of the components.

The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but are not limited. to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many others. The most catalytically interesting ionic liquids for acid catalysis are those derived from ammonium halides and Lewis acids (such as $AlCl_3$, $TiCl_4$, $SnCl_4$, $FeCl_3$, etc.). Chloroaluminate ionic liquids are perhaps the most commonly used ionic liquid catalyst systems for acid-catalyzed reactions.

Examples of such low temperature ionic liquids or molten fused salts are the chloroaluminate salts. Alkyl imidazolium or pyridinium chlorides, for example, can be mixed with aluminum trichloride ($AlCl_3$) to form the fused chloroaluminate salts.

The processes as described herein can employ a catalyst composition comprising at least one aluminum halide such as aluminum chloride, at least one quaternary ammonium halide and/or at least one amine halohydrate, and at least one cuprous compound. Such a catalyst composition and its preparation is disclosed in U.S. Pat. No. 5,750,455, which is incorporated by reference in its entirety herein.

Alternatively, the ionic liquid catalyst can be a chloroaluminate ionic liquid catalyst. For example, the chloroaluminate ionic liquid catalyst can be a pyridinium-based chloroaluminate ionic liquid catalyst, an imidazolium-based chloroaluminate ionic liquid catalyst, and mixtures thereof. These ionic liquids have been found to be much more effective in the alkylation of isopentane with ethylene than aliphatic ammonium chloroaluminate ionic liquid (such as tributyl-methyl-ammonium chloroaluminate).

The chloroaluminate ionic liquid catalyst can be: (1) a chloroaluminate ionic liquid catalyst comprising a hydrocarbyl substituted pyridinium halide of the general formula A below and aluminum trichloride or (2) a chloroaluminate ionic liquid catalyst comprising a hydrocarbyl substituted imidazolium halide of the general formula B below and aluminum trichloride. Such a chloroaluminate ionic liquid catalyst can be prepared by combining 1 molar equivalent hydrocarbyl substituted pyridinium halide or hydrocarbyl substituted imidazolium halide with 2 molar equivalents aluminum trichloride. The ionic liquid catalyst can also be (1) a chloroaluminate ionic liquid catalyst comprising an alkyl substituted pyridinium halide of the general formula A below and aluminum trichloride or (2) a chloroaluminate ionic liquid catalyst comprising an alkyl substituted imidazolium halide of the general formula B below and aluminum trichloride. Such a chloroaluminate ionic liquid catalyst can be prepared by combining 1 molar equivalent alkyl substituted pyridinium halide or alkyl substituted imidazolium halide with 2 molar equivalents of aluminum trichloride.

wherein R=H, methyl, ethyl, propyl, butyl, pentyl or hexyl group and X is a haloaluminate, and $R_1$ and $R_2$=H, methyl, ethyl, propyl, butyl, pentyl, or hexyl group and where $R_1$ and $R_2$ may or may not be the same. In one embodiment, the haloaluminate is a chloroaluminate. The ionic liquid catalyst can also be mixtures of these chloroaluminate ionic liquid catalysts.

Other examples of suitable chloroaluminate ionic liquid catalysts are 1-butyl-4-methyl-pyridinium chloroaluminate (BMP), 1-butyl-pyridinium chloroaluminate (BP), 1-butyl-3-methyl-imidazolium chloroaluminate (BMIM), 1-H-pyridinium chloroaluminate (HP), and N-butylpyridinium chloroaluminate ($C_5H_5NC_4H_9Al_2Cl_7$), and mixtures thereof A metal halide may be employed as a co-catalyst to modify the catalyst activity and selectivity. Commonly used halides for such purposes include NaCl, LiCl, KCl, $BeCl_2$, $CaCl_2$, $BaCl_2$, $SiCl_2$, $MgCl_2$, $PbCl_2$, CuCl, $ZrCl_4$, and AgCl as published by Roebuck and Evering (Ind. Eng. Chem. Prod. Res. Develop., Vol. 9, 77, 1970), which is incorporated by reference in its entirety herein. Especially useful metal halides are CuCl, AgCl, $PbCl_2$, LiCl, and $ZrCl_4$. Another useful metal halide is $AlCl_3$.

HCl or any Broensted acid may be employed as an effective co-catalyst to enhance the activity of the catalyst by boosting the overall acidity of the ionic liquid-based catalyst. The use of such co-catalysts and ionic liquid catalysts that are useful in practicing the present process are disclosed in U.S. Published Patent Application Nos. 2003/0060359 and 2004/0077914, the disclosures of which are herein incorporated by reference in their entirety. Other co-catalysts that may be used to enhance the catalytic activity of the ionic liquid catalyst include IVB metal compounds. In one embodiment, the co-catalysts include IVB metal halides such as $TiCl_3$, $TiCl_4$, $TiBr_3$, $TiBr_4$, $ZrCl_4$, $ZrBr_4$, $HfC_4$, and $HfBr_4$ as described by Hirschauer et al. in U.S. Pat. No. 6,028,024, which document is incorporated by reference in its entirety herein.

The following examples are provided to further illustrate the present processes and advantages thereof. The examples are meant to be only illustrative, and not limiting.

EXAMPLES

Example 1

Preparation of N-butylpyridinium Chloroaluminate Catalyst

N-butylpyridinium chloroaluminate ($C_5H_5NC_4H_9Al_2Cl_7$) ionic liquid catalyst was purchased. The catalyst had the following composition.

| | |
|---|---|
| Wt % Al | 12.4 |
| Wt % Cl | 56.5 |
| Wt % C | 24.6 |
| Wt % H | 3.2 |
| Wt % N | 3.3 |

Example 2

$C_4$ Olefin and Isobutane Alkylation $C_4$ olefin alkylation with isobutane was performed in a 100 cc continuously stirred tank reactor. A mixture of isobutane and 2-butene having a 8:1 molar ratio was fed to the reactor while vigorously stirring at 1600 RPM. The chloroaluminate ionic liquid catalyst of Example 1 was fed to the reactor via a second inlet port targeting to occupy 8 vol % in the reactor. A small amount of anhydrous HCl gas was added to the process. The average residence time (combined volume of feeds and catalyst) was about 8 minutes. The outlet pressure was maintained at 100 psig using a backpressure regulator. The reactor temperature was maintained at 0° C. using external cooling. The reactor effluent was separated in a 3-phase separator into $C_4$— gas, an alkylate hydrocarbon phase, and the ionic liquid catalyst. The ionic liquid catalyst was recycled back to the reactor continuously. The amount of catalyst in the system was about 220 g, and the catalyst circulation was 100 g/hour. After 19 hours of continuous operation, approximately 20 cc of the used catalyst was drained, and 20-30 g of fresh catalyst was added. The draining of used catalyst and addition of fresh catalyst were repeated at 33, 36, 43, 57 and 75 hours. The run was stopped after 81 hours on stream.

Example 3

Measurement of Properties of Fresh and Used Catalyst

The total acidity of the fresh catalyst used in Example 2 and the used catalyst drained in Example 2 was determined using an acid/base titration method as follows. An automatic potentiometric titrator was set up using 100 mL of nitrogen purged, de-aerated water and isopropyl alcohol mixture in a beaker. The solution in the beaker was blanketed with dry nitrogen gas and stirred. Using an airtight syringe, a catalyst sample was drawn to transfer approximately 0.05 g into the beaker. The weight charged to the beaker was determined by difference to the nearest 0.0001 g. The catalyst sample charged to the beaker dissolved in the water/isopropyl mixture rapidly, and the pH value of the solution decreased. The resulting solution was titrated with standardized 0.1 N KOH solution to the same potential as the blank. A well-defined inflection point was shown in the resulting titration curve around pH 7. From the amount of KOH solution consumed for the titration, the total acidity was calculated as milligram equivalent of KOH (meq) required to titrate one gram of catalyst to a specified end point. Relative acidity was calculated as percent retention of acidity from the fresh ionic liquid catalyst.

The density of the fresh catalyst used in Example 2 and the used catalyst drained in Example 2 was measured in a glove box using a 10 ml volumetric flask and a four decimal point balance.

The aluminum content of the fresh catalyst used in Example 2 and the used catalyst drained in Example 2 was measured using an ICP method. Since the samples were moisture sensitive, the weighing was done in a glove box.

Table 1 provides the total acidity, relative acidity, density, and aluminum content of the fresh catalyst used in Example 2 and the used catalyst drained in Example 2.

TABLE 1

| | Total Acidity, meq OH/g catalyst | Relative acidity, % | Density, g/cc | Wt % Al |
|---|---|---|---|---|
| Fresh Catalyst | 696 | 100 | 1.320 | 12.07 |
| Used Catalyst Sample #1 | — | — | 1.303 | 10.83 |
| Used Catalyst Sample #2 | 580 | 83.3 | 1.261 | 11.25 |
| Used Catalyst Sample #3 | 644 | 92.5 | 1.259 | 11.72 |
| Used Catalyst Sample #4 | 650 | 93.4 | 1.290 | 11.49 |
| Used Catalyst Sample #5 | 590 | 84.8 | 1.242 | 10.4 |
| Used Catalyst Sample #6 | 572 | 82.1 | 1.210 | 9.64 |
| Used Catalyst Sample #7 | 512 | 73.6 | 1.211 | 9.4 |

Example 4

Catalyst Deactivation Based on Total Acidity

Figure 1:
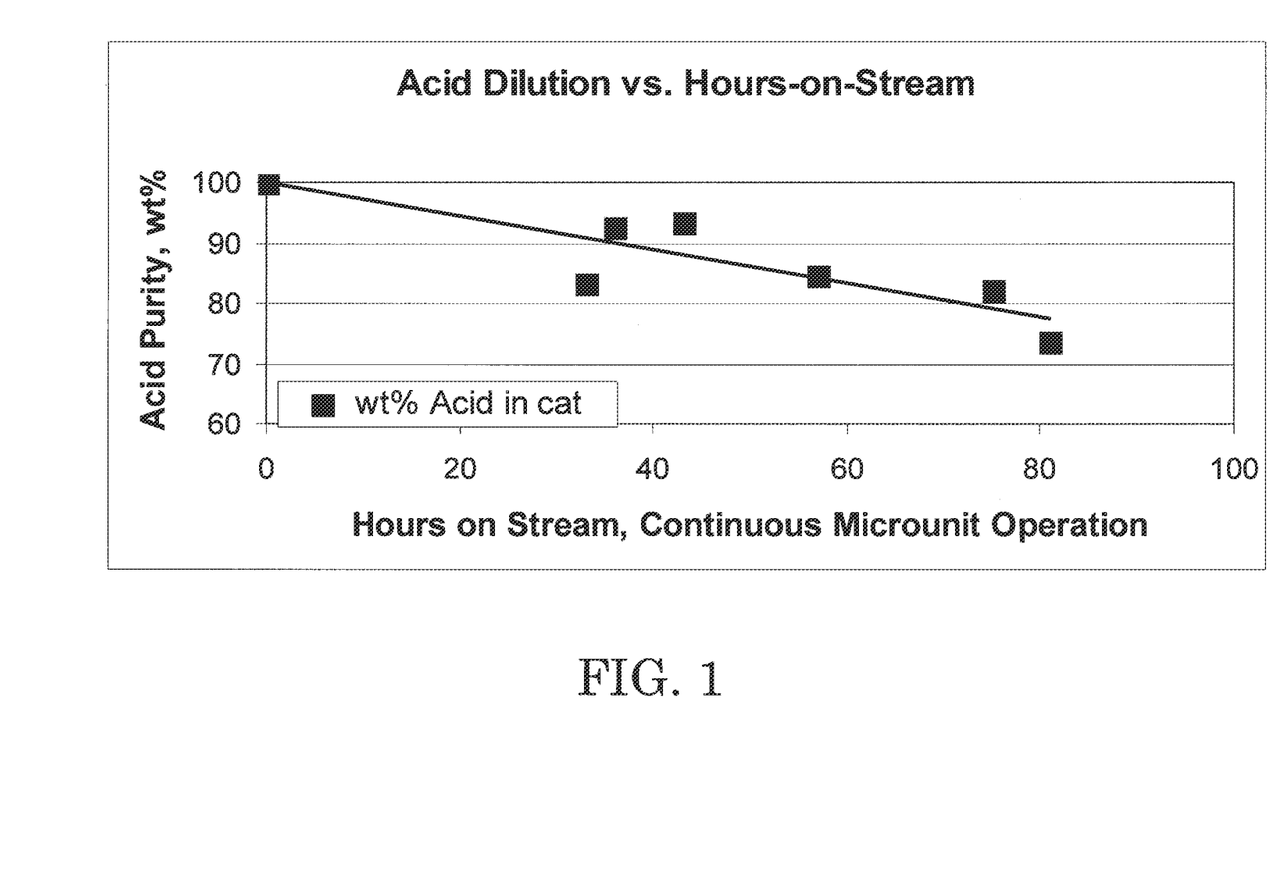
FIG. 1 is a graph depicting deactivation of a chloroaluminate ionic liquid catalyst, in terms of total acidity, as a function of time.

FIG. 1 shows catalyst deactivation, based on total acidity and as a function of hours on stream, as determined in Example 3. As the catalyst was deactivated upon extended operation, undesirable oligomeric by-product yield in the alkylate gasoline increased. To maintain alkylation reaction selectivity, the total acidity of the catalyst should be maintained at >80% of the initial acidity.

Example 5

Catalyst Deactivation Based on Density

Figure 2:
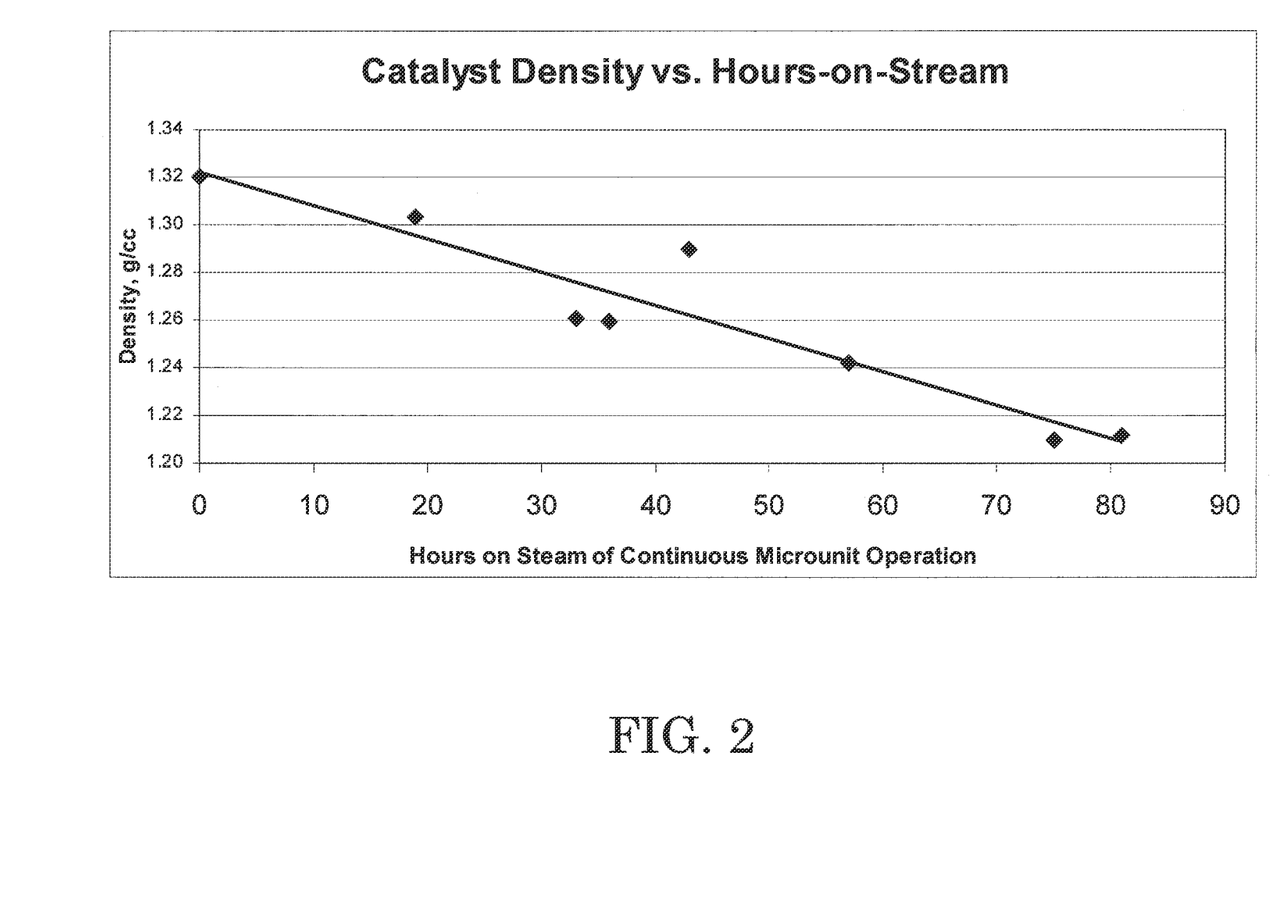
FIG. 2 is a graph depicting deactivation of a chloroaluminate ionic liquid catalyst, in terms of density, as a function of time.

FIG. 2 shows catalyst deactivation, based on density and as a function of hours on stream, as determined in Example 3. To maintain alkylation reaction selectivity, the density of the catalyst should be maintained at >1.21 g/cc.

Example 6

Catalyst Deactivation Based on Aluminum Content

Figure 3:
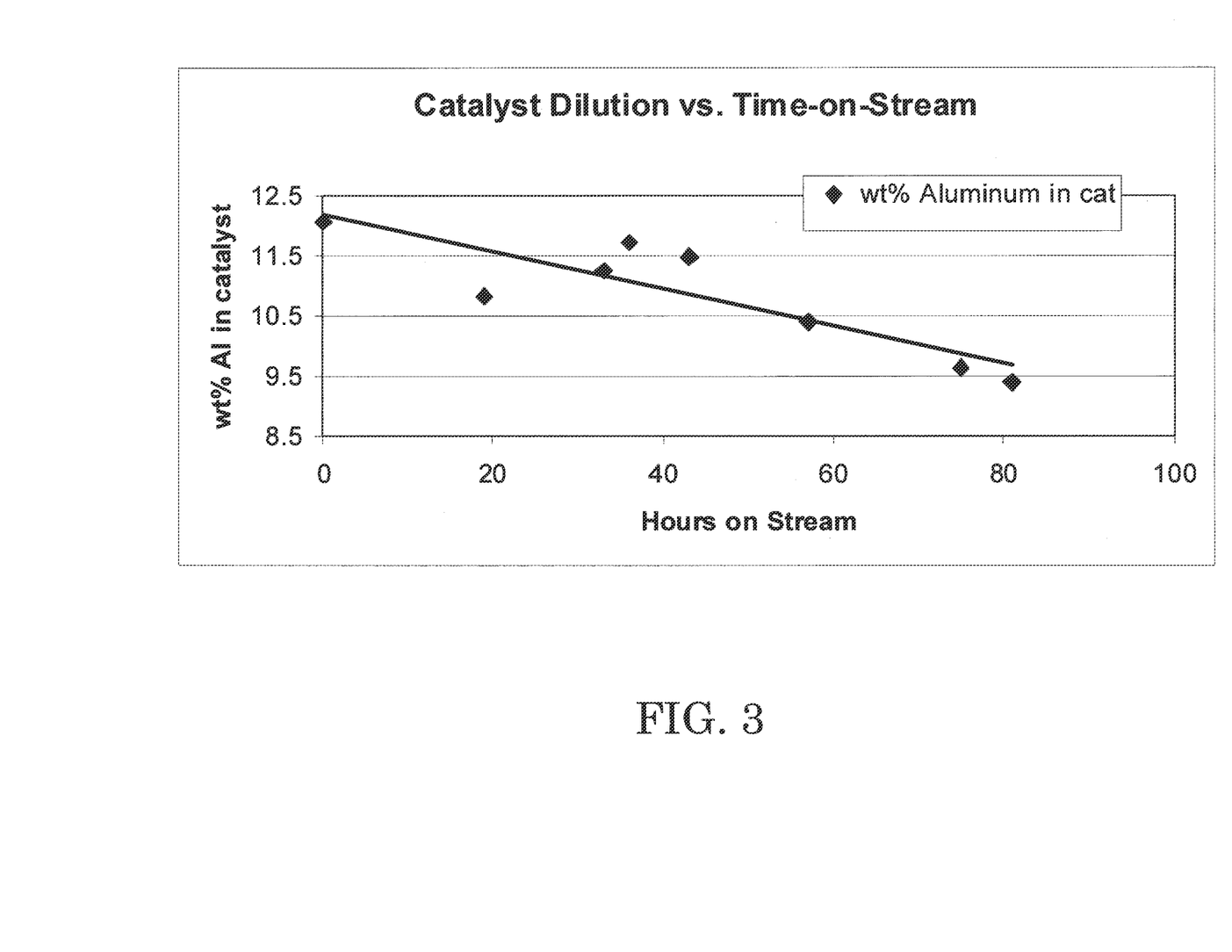
FIG. 3 is a graph depicting deactivation of a chloroaluminate ionic liquid catalyst, in terms of aluminum content, as a function of time.

FIG. 3 shows catalyst deactivation, based on aluminum content and as a function of hours on stream, as determined in Example 3. To maintain alkylation reaction selectivity, the aluminum content of the catalyst should be maintained at >9.5 wt % Al.

Although the present processes have been described in connection with specific embodiments thereof, it will be appreciated by those skilled in the art that additions, deletions, modifications, and substitutions not specifically described may be made without departing from the spirit and scope of the processes as defined in the appended claims.

That which is claimed is:

1. A process for determining ionic liquid catalyst deactivation, comprising:
   (a) collecting at least one sample of an ionic liquid catalyst;
   (b) hydrolyzing the at least one sample to provide at least one hydrolyzed sample including protons;
   (c) titrating the at least one hydrolyzed sample with a basic reagent until the basic reagent neutralizes a Lewis acid species of the ionic liquid catalyst, as indicated by an indicator, to determine a volume of the basic reagent necessary to neutralize the Lewis acid species of the ionic liquid catalyst; and
   (d) calculating an acid content of 512 meq OH/g or greater of the at least one sample from the volume of basic reagent determined in step (c); wherein the acid content is greater than 80% of an initial acid content of a fresh ionic liquid catalyst.

2. The process according to claim 1, further comprising (e) comparing the acid content of the at least one sample to a predetermined value.

3. The process according to claim 2, wherein the predetermined value is the initial acid content of the fresh ionic liquid catalyst that has not been subject to deactivation.

4. The process according to claim 1, wherein the ionic liquid catalyst is a partially deactivated ionic liquid catalyst.

5. The process according to claim 4, wherein the partially deactivated ionic liquid catalyst has been used to catalyze a Friedel-Crafts reaction.

6. The process according to claim 5, wherein the Friedel-Crafts reaction is alkylation.

7. The process according to claim 1, wherein the ionic liquid catalyst is a fresh ionic liquid catalyst having a total acidity greater than 650 meq OH/g.

8. The process according to claim 7, wherein the fresh ionic liquid catalyst is newly synthesized.

9. The process according to claim 1, wherein the at least one sample is a plurality of samples collected at regular intervals from a reaction employing the ionic liquid catalyst.

10. The process according to claim 1, wherein the at least one sample collected in step (a) is less than 1 gram.

11. The process according to claim 1, wherein the basic reagent is a hydroxide of a Group IA metal.

12. The process according to claim 1, wherein the ionic liquid catalyst is a pyridinium-based chloroaluminate ionic liquid catalyst.

13. The process according to claim 1, wherein the ionic liquid catalyst is selected from the group consisting of:
   a first chloroaluminate ionic liquid catalyst comprising a hydrocarbyl substituted pyridinium halide of the general formula A and aluminum trichloride; and
   a second chloroaluminate ionic liquid catalyst comprising an alkyl substituted imidazolium halide of the general formula B and aluminum trichloride;
   wherein the general formula A and the general formula B are represented by the structures:

(A)

(B)

where R=-butyl, X is a haloaluminate, $R_1$ and $R_2$=-butyl group.

14. The process according to claim 1, wherein the ionic liquid catalyst is N-butylpyridinium chloroaluminate ($C_5H_5NC_4H_9Al_2Cl_7$).

15. The process according to claim 2, wherein the predetermined value is greater than 650 meq OH/g.

16. The process according to claim 1, further comprising repeating steps (a) to (d) and maintaining the acid content of the at least one samples at greater than 80% of the initial acid content of the fresh ionic liquid catalyst that has not been subject to deactivation.

17. The process according to claim 16, wherein the initial acid content of the fresh ionic liquid catalyst that has not been subject to deactivation has a total acidity greater than 650 meq OH/g.

18. The process according to claim 1, wherein the titrating is done within an hour of the collecting.

19. The process according to claim 1, wherein the acid content of the at least one sample is 572 meq OH/g or greater.

20. The process according to claim 1, wherein the hydrolyzing and the titrating are performed in a same beaker.

21. The process according to claim 1, wherein the basic reagent is selected from the group consisting of sodium hydroxide, potassium hydroxide, rubidium hydroxide, cesium hydroxide, and barium hydroxide.

22. The process according to claim 21, wherein the basic reagent is selected from the group consisting of potassium hydroxide, rubidium hydroxide, cesium hydroxide, and barium hydroxide.

23. The process according to claim 1, wherein the hydrolyzing is done using nitrogen purged, de-aerated water and an alcohol.

24. The process according to claim 1, wherein the ionic liquid catalyst is prepared by combining 1 molar equivalent alkyl substituted pyridinium halide or alkyl substituted imidazolium halide with 2 molar equivalents of aluminum trichloride.

* * * * *